United States Patent
Moscaritolo

(10) Patent No.: US 6,855,249 B2
(45) Date of Patent: *Feb. 15, 2005

(54) PROGNOSTIC HEALTH MONITORING OF FLUIDIC SYSTEMS USING MEMS TECHNOLOGY

(75) Inventor: Daniel Moscaritolo, Newbury Park, CA (US)

(73) Assignee: PTI Technologies, Inc., Oxnard, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/818,248

(22) Filed: Apr. 5, 2004

(65) Prior Publication Data

US 2004/0188331 A1 Sep. 30, 2004

Related U.S. Application Data

(60) Continuation of application No. 10/259,905, filed on Sep. 27, 2002, now Pat. No. 6,736,980, which is a division of application No. 09/721,499, filed on Nov. 22, 2000, now Pat. No. 6,471,853.

(51) Int. Cl.[7] ............................................ B01D 35/143
(52) U.S. Cl. ............................ 210/90; 210/87; 210/93; 210/321.6; 96/4; 96/417
(58) Field of Search ............................... 210/85, 87, 90, 210/93, 103, 143, 321.6, 321.69, 636, 637, 650, 739, 741; 95/19, 23, 45; 96/4, 417, 420–422; 73/53.01, 53.05, 61.41, 61.47; 702/340

(56) References Cited

U.S. PATENT DOCUMENTS

| | | | | |
|---|---|---|---|---|
| 2,942,572 A | * | 6/1960 | Pall | 116/267 |
| 3,262,565 A | * | 7/1966 | Silverwater | 210/90 |
| 5,096,574 A | * | 3/1992 | Birdsong et al. | 210/90 |
| 5,163,920 A | * | 11/1992 | Olive | 604/247 |
| 5,702,592 A | * | 12/1997 | Suri et al. | 210/90 |
| 5,788,468 A | * | 8/1998 | Dewa et al. | 417/415 |
| 5,883,310 A | * | 3/1999 | Ho et al. | 73/766 |
| 5,968,371 A | * | 10/1999 | Verdegan et al. | 210/739 |
| 6,009,404 A | * | 12/1999 | Eimer | 705/7 |
| 6,030,525 A | * | 2/2000 | Eimer et al. | 210/98 |
| 6,051,144 A | * | 4/2000 | Clack et al. | 210/739 |
| 6,071,819 A | * | 6/2000 | Tai et al. | 438/694 |
| 6,076,392 A | * | 6/2000 | Drzewiecki | 73/23.2 |
| 6,077,422 A | * | 6/2000 | Ryles | 210/108 |
| 6,077,435 A | * | 6/2000 | Beck et al. | 210/636 |
| 6,286,363 B1 | * | 9/2001 | Discenzo | 73/53.01 |
| 6,334,959 B1 | * | 1/2002 | Sutton et al. | 210/767 |
| 6,471,853 B1 | * | 10/2002 | Moscaritolo | 210/85 |
| 6,537,444 B2 | | 3/2003 | Wilberscheid et al. | |
| 2003/0047517 A1 | | 3/2003 | Schoess | |

FOREIGN PATENT DOCUMENTS

| WO | WO 0150106 | 7/2001 |
|---|---|---|
| WO | WO 0152185 | 7/2001 |

OTHER PUBLICATIONS

Aerospace Engineering, Jan./Feb. 1994, "Hydraulic System Diagnostic Sensors", pp. 43–48.*

Http://www.transtonics.com/zprimer.htm: Pressure Transducer Basics: A Primer, Nov. 20, 2000, pp. 1 of 13.*

* cited by examiner

*Primary Examiner*—Joseph Drodge
(74) *Attorney, Agent, or Firm*—Pillsbury Winthrop LLP

(57) ABSTRACT

The present invention is directed to a filter module that may incorporate sensors to measure various characteristics of fluid flow and filtration. The sensors may be MEMS and may measure the temperature, flow rate, pressure, etc. of the fluid. One or more MEMS sensors may be included in a sensor package which, in turn, may be included in a sensor component. The latter, which may also include a processor, conductor pins, etc. for data communication, may be coupled to a sensor port in such a way as to allow contact between the sensor(s) and the fluid. Sensor measurements may be used to determine the occurrence of harmful events, such as cavitation or particle breakthrough, or to predict the remaining service life of a filter element.

44 Claims, 7 Drawing Sheets

PROGNOSTIC HEALTH MONITORING OF FLUIDIC SYSTEMS USING MEMS TECHNOLOGY

RELATED APPLICATION DATA

This is a continuation of application Ser. No. 10/259,905, filed Sep. 27, 2002, now U.S. Pat. No. 6,736,980, is a divisional of application Ser. No. 09/721,499, filed Nov. 22, 2000, now U.S. Pat. No. 6,471,853.

FIELD OF INVENTION

The present invention is directed to filtration elements incorporating micro-electro-mechanical systems (MEMS) to provide flow and filtration characteristic data.

BACKGROUND

In previous applications, filter modules have been used in a variety of applications and fluidic environments. When in service, it is often desirable to sense various fluid flow and filter performance characteristics in order to determine whether a filter element within the filter module is performing within application specifications and whether a filter element must be replaced or reconditioned before continuing operation.

In typical filter modules, a filter element is encased within a filter body and between inlet and outlet end caps. A filter manifold(s) may be attached to the filter body to feed unfiltered medium to the upstream side of the filter element (e.g., where the filter element is cylindrical, the outside of the filter element). As the medium passes to the downstream side of the filter element through the membrane material, contaminants are removed from the medium. Filtered medium is then collected from the downstream side of the filter element (e.g., where the filter element is cylindrical, the inside of the filter element).

During the filter element's service life, an increasing amount of removed contaminant will collect on one side of the filter element in a phenomenon known as fouling. Fouling causes the pressure difference between the upstream and downstream sides of the filter element to increase and thereby lowers the filtration efficiency of the filter element. If the differential pressure exceeds a certain value that is dependent upon the filter element material and design, the filter element may be damaged. Additionally, at high differential pressures, particle breakthrough (i.e., contaminant particles passing through the pores in the filter element) may occur.

In prior modules, the filter head may have contained conventional pressure transducers, differential pressure sensors, virtual pressure switches and temperature detectors to measure characteristics of fluid flow and filter performance. These components were used to sense the pressure differential across the filter element to determine whether the filter element was sufficiently clogged with contaminant removed from the fluid flow to require replacement. These pressure sensors were generally binary in nature, i.e., they either indicated that the filter element needed to be replaced (e.g., by causing a part to pop up out of exterior of the filter head) or that it was still useable.

The use of the pressure-sensing components used in traditional filter modules is often a significant design constraint in weight- and size-sensitive applications, e.g., aircraft filtration systems. Moreover, traditional filter modules offer no means for predicting when a filter element will need to be replaced. Finally, traditional filter modules disturb or alter fluid flow by requiring that pressure-sensing components be inserted into the stream of flow, creating turbulence.

DETAILED DESCRIPTION

Embodiments of the present invention are directed to filter modules incorporating MEMS sensors to measure fluid flow or filter performance characteristics. Various MEMS sensors for measuring pressure, differential pressure, flow rate, temperature, pH level and/or moisture content of the fluid flow may be used. Multiple MEMS sensors may be arranged on a single chip. The MEMS sensors may output real-time measurements or related data and these measurements or data may be interpreted to predict when failure of the filter element will occur or to determine whether replacement of the filter element is necessary. In particular embodiments, MEMS sensor data may be used to detect the occurrence of undesirable events such as particle breakthrough or cavitation.

Figure 1A:
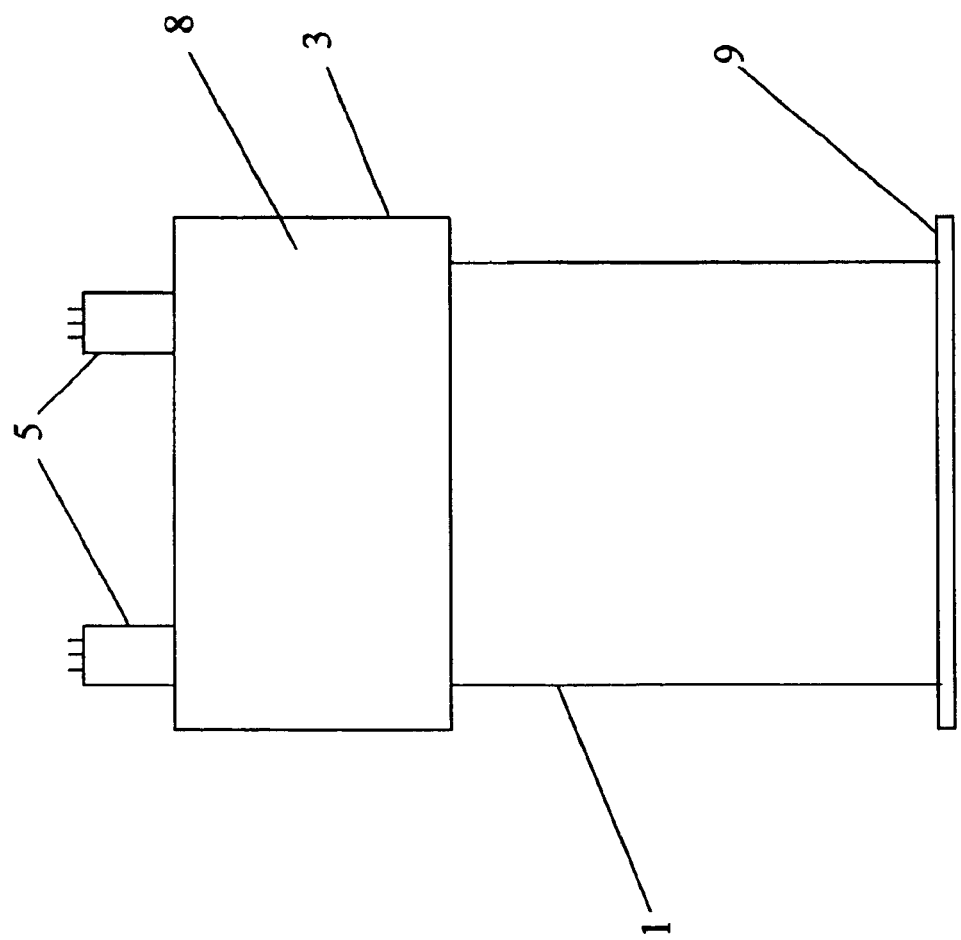
FIG. 1A depicts a filter module according to an embodiment of the present invention.
Figure 1B:
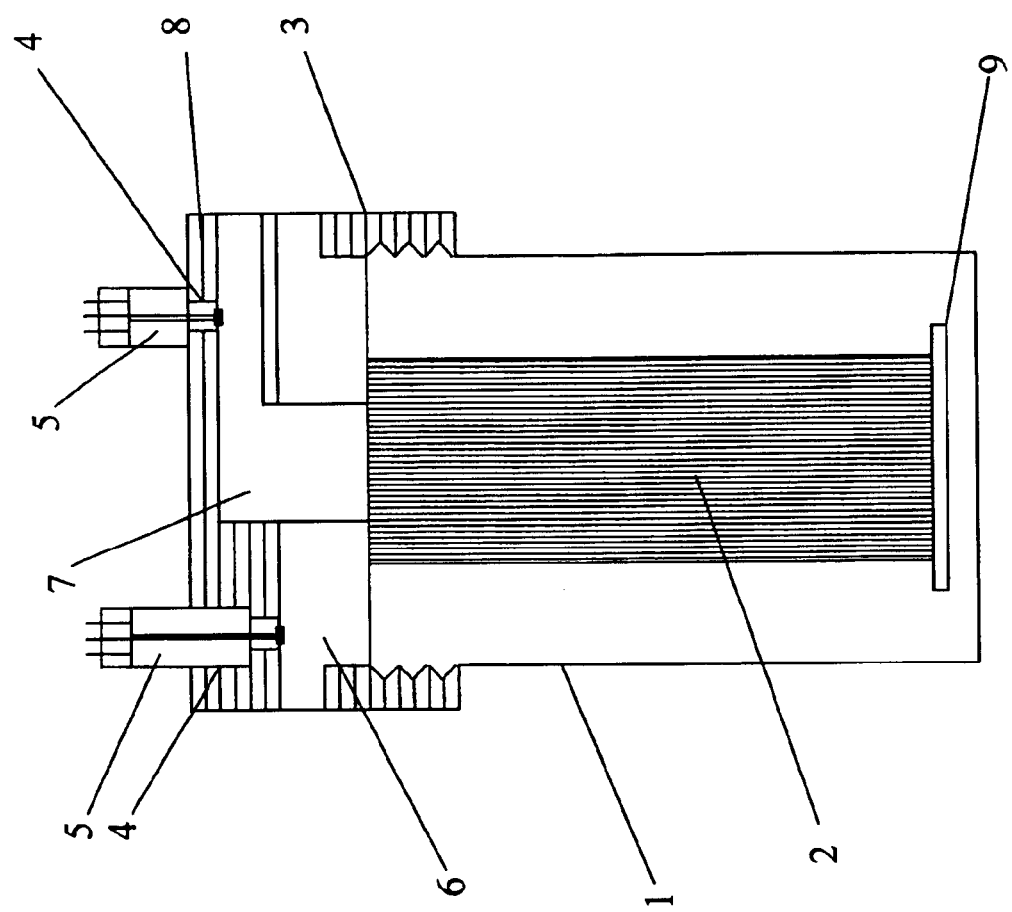
FIG. 1B depicts a cut-away view of the filter module shown in FIG. 1A.

FIGS. 1A and 1B illustrate a filter module according to an embodiment of the present invention. The filter module may include a filter body 1, a filter element 2, and a filter manifold 3. The filter manifold 3 may have one or more sensor ports 4 in which one or more sensor components 5a and 5b (collectively sensor components 5) may be mounted. Sensor components 5 are described in greater detail in the ensuing discussion related to FIG. 2. The filter manifold 3 may have one or more inlet fluid flow cavities 6 and one or more outlet fluid flow cavities 7. The sensor ports 4 may extend through the housing 8 of the filter manifold 3. The interface between each sensor port 4 and the corresponding sensor component 5 may be fluid-tight.

The filter module shown in FIGS. 1A and 1B is configured for dead-end flow. Accordingly, the filter body 1 may have an end cap 9 attached to one end (the dead end). In alternative embodiments, the filter module may be configured for through-flow or cross-flow. In such configurations, the filter module may have more than one filter manifold 3. The shape and location of the inlet fluid flow cavity 6 and the outlet fluid flow cavity 7 may depend upon a number of factors, including the desired flow characteristics of the unfiltered or filtered fluid, the size and shape of the filter element 2 and filter body 1, the fluid being filtered, and the like.

The sensor ports 4 and sensor components 5 may be arranged to measure flow and filtration characteristics at points of interest. For example, in embodiments of the invention, a sensor port 4 and sensor component 5 may be positioned in at least one of the inlet fluid flow cavities 6 and in at least one of the outlet fluid flow cavities 7. If each sensor component 5 includes a pressure sensor, then the difference between the readings of the pressure sensors at the inlet fluid flow cavity 6 and the outlet fluid flow cavity 7 may be used to approximate the differential pressure across the membrane of the filter element 2. In other embodiments, sensor components 5 may be placed at points likely to experience turbulent flow or fouling. Although sensor components 5 are shown as connected to sensor ports 4 in the filter manifold 3, a person of ordinary skill in the art will readily understand that sensor components 5 may be located in sensor ports 4 in the filter body 1, the end cap 9, or other parts of the filter module.

The sensor component 5 and the sensor port 4 may be coupled together either removably or fixedly. In embodiments of the invention, the sensor component 5 may be removably coupled to the sensor port 4, using threads (as shown in FIG. 1B), a slide-locking mechanism, a spring or retaining clip, or the like. In alternative embodiments, the sensor component 5 may be fixedly attached to the sensor port 4 by welding, bonding or other means. In still other embodiments, the sensor component 5 may be integrated into the housing 8 of the filter manifold 3 to form a unitary part.

Sensor components 5 and/or sensor ports 4 may include auto-configuration features to ensure that the correct sensor component 5 is properly oriented in the sensor port 4. For example, the sensor component 5 may have a protrusion that fits into a notch in the sensor port. In a preferred embodiment, the sensor component 5 and the sensor port 4 may have a configuration sensor to indicate that that the sensor component 5 is properly aligned. For example, the sensor port 4 and sensor module 5 may include a segment of conductive material having two ends. Electrical power may be applied to one of the segments. When the segments are properly aligned (indicating proper orientation of the MEMS sensor package 101), the segments may complete an electrical circuit and current may flow through the segments, creating a signal indicating proper orientation.

In an alternative embodiment, a sensor port may be located in the end cap 9. A sensor component capable of measuring differential pressure may be coupled to said sensor port. One surface of the differential pressure sensor may be exposed to the fluid inside the filter element 2 while a second surface of the differential pressure sensor may be exposed to fluid outside the filter element 2 contained in the filter body 1.

In another embodiment, measurements from the MEMS sensor package 101 itself may be used as auto-configuration features to verify that the sensor component is of the proper variety and is properly oriented. Measurement data from the MEMS sensor package 101 may be tagged with an identification or verification code unique to the filter module, manufacturer, or user. In an embodiment of the invention, the MEMS sensor package may include redundant temperature sensors, which may be used to determine the position of each temperature sensor (upstream or downstream) in relation to a flow rate sensor using thermal characteristics of the fluid flow. Comparison of the measurement data from these temperature sensors may indicate the orientation of the MEMS sensor package 101 in relation to the fluid flow direction.

A software lock-out may prevent collection of measurement data from the MEMS sensor package until the auto-configuration features indicate that a proper sensor component 5 has been mounted in the sensor port 4 in the proper orientation. This may ensure that the system is not operated in a way that may damage the sensor component 5 (and specifically, the MEMS sensor package 101) or that will lead to inaccurate measurement (as explained in greater detail below).

Figure 2:
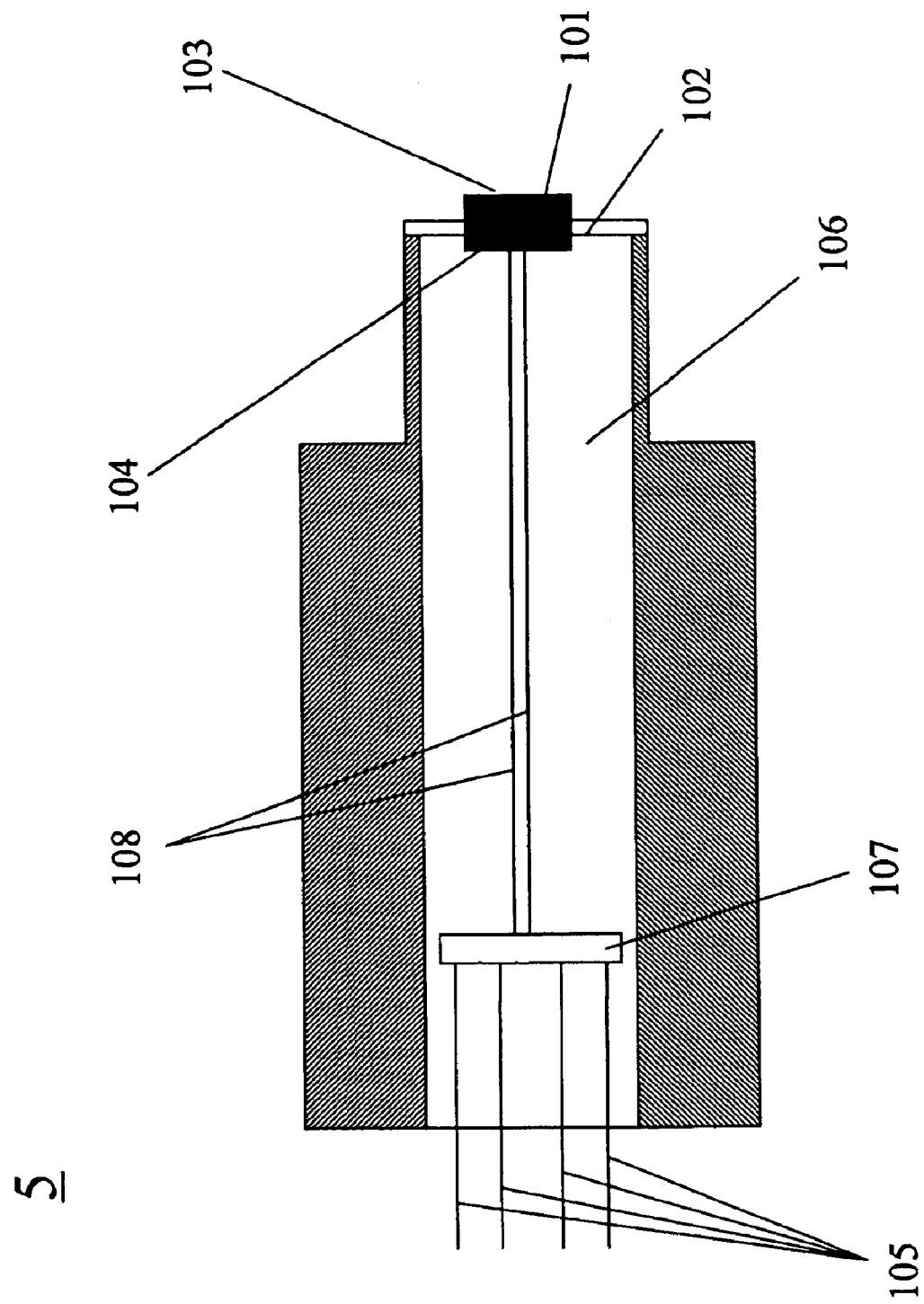
FIG. 2 depicts a sensor component according to an embodiment of the present invention.
Figure 3:
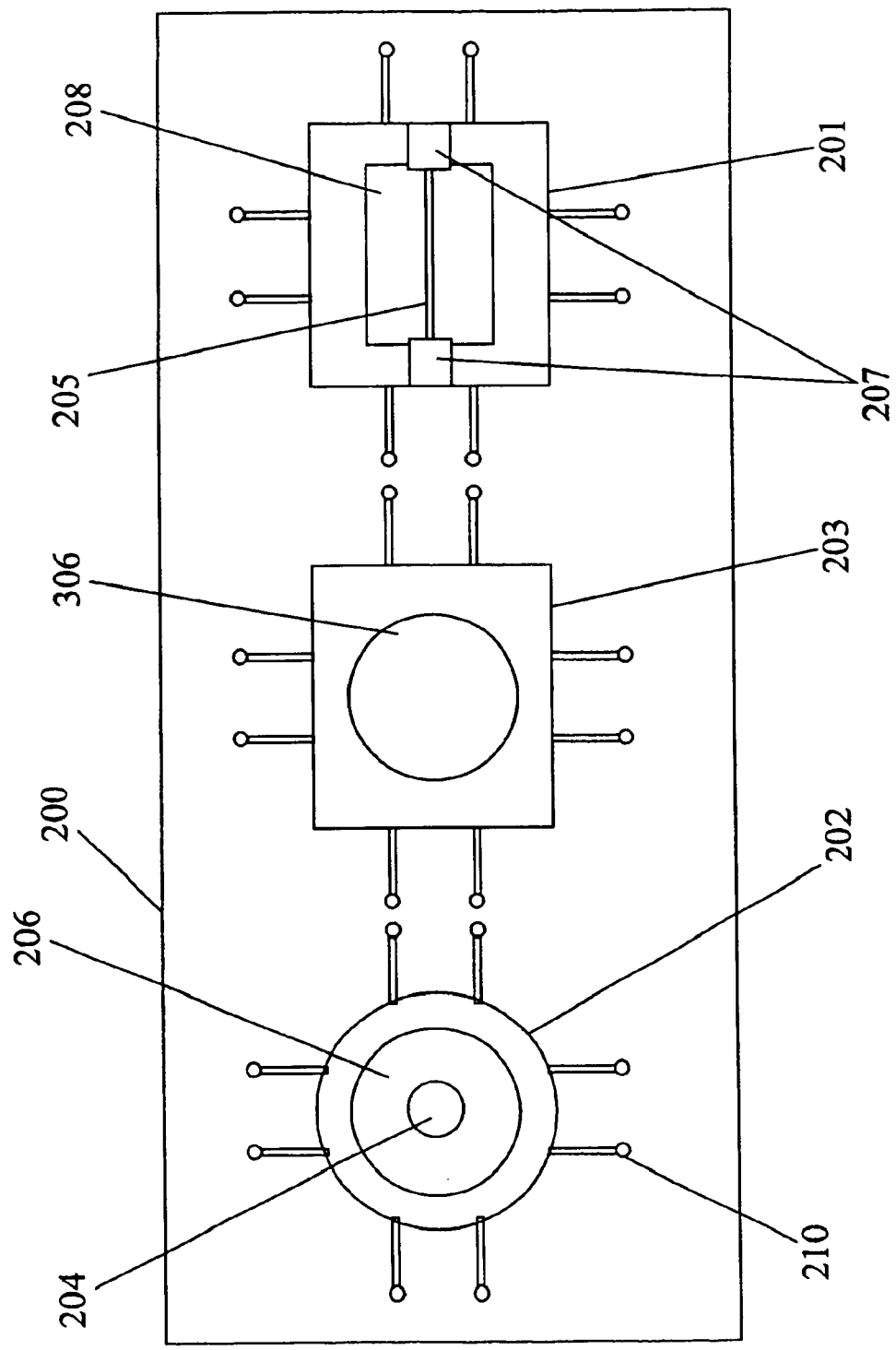
FIG. 3 illustrates a top view of single-chip embodiment of a MEMS sensor package.
Figure 6:
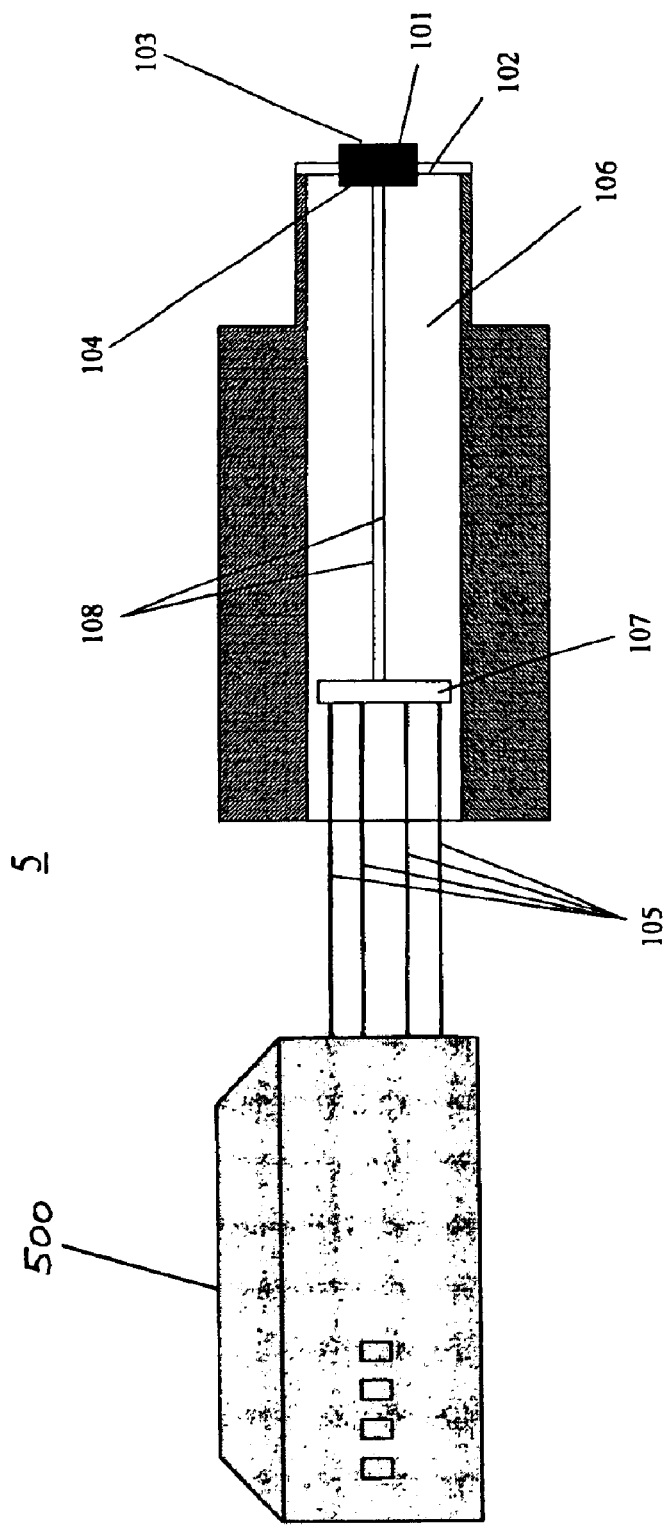
FIG. 6 shows a health monitoring system according to an embodiment of the present invention.

As shown in FIG. 2, the sensor component 5 may include one or more MEMS sensors in a MEMS sensor package 101, which may be combined onto a single chip (as shown in FIG. 3). The MEMS sensor package 101 may be used to measure the flow rate of the fluid through the filter module, the temperature of the fluid and the pressure of the fluid. The MEMS sensor package 101 may be embedded in a seal 102 at one end of the sensor component 5 so that the front face 103 of the MEMS sensor package 101 will be exposed to the fluid flow when the sensor component 5 is properly oriented within the sensor port 4. The back face 104 of the MEMS sensor package 101 may be exposed to an interior conduit 106. In an embodiment of the invention, the back face 104 may have an opening through which electrical conductors 108 may be passed to contact conductive surface features of the MEMS sensor package 101. The electrical conductors 108 may be attached to a processor 107 so that the MEMS sensor package 101 may communicate measurement data to the processor 107. In turn, the processor 107 may be attached to conductive pins 105 that may, for example, be used to communicate data related to the MEMS sensor package 101 measurements to a central computer or other data processing device 500 (see FIG. 6). The conductive pins 105 may be configured to be attached to standard data transmission cables. In an alternative wireless embodiment of the invention, the MEMS sensor package 101 may be electrically connected to a transmitter and the processor 107 may be used to convert the measurement data into a transmittable form.

In embodiments of the invention, an outside triggering signal may be sent to the processor 107. When the triggering signal is received, the processor 107 may take a measurement data reading from the MEMS sensor package 101. Triggering signals may be sent periodically. In embodiments of the invention, the processor 107 may be programmed with a triggering level. The triggering level may be related to a time interval, a measurement data reading level or the like. For example, in systems in which sensor measurement data is periodically collected, the processor 107 may be programmed with the time interval at which MEMS sensor package 101 measurement data is to be collected or transmitted/communicated to a central computer. As another example, the processor 107 may be programmed with a pressure trigger level such that, if the pressure reading from the MEMS sensor package 101 is greater than the pressure trigger level, data related to the MEMS sensor package 101 measurement data may be transmitted or communicated to the central computer.

It is preferable that the sensor components do not impede or disturb flow of the medium through the filter module. Accordingly it is desirable that the sensor components 5 be placed in the sensor ports 4 so that the front face 103 of the MEMS sensor package 101 is flush with the interior surface of the housing 8 or other part that the sensor port 4 penetrates.

FIG. 3 shows an embodiment of a MEMS sensor package according to the present invention. The MEMS sensor package 101 may include a flow rate sensor 201, a temperature sensor 202 and a pressure sensor 203. The sensors may be mounted on a chip 200 made of silicon or other semiconductive material. Each sensor may include one or more conductive leads 210 which may be electrically connected to conductors 108. The arrangement of the sensors may be changed to suit a particular application and need not be a linear arrangement. Moreover, a MEMS sensor package 101 may contain redundant sensors.

The temperature sensor 202 may consist of a resistive element 204 whose resistance is dependent on its temperature. A known current may be passed through the resistive element 204 and the voltage drop across the resistive element 204 may be measured. The resistive element 204 may be made of a material whose resistance is highly sensitive to temperature so that relatively little power must be supplied to the resistive element to achieve noticeable differences between the voltage drops across the resistive element 204 at two different temperatures. Moreover, the material may be chosen so that the relationship between resistance or output voltage and temperature is strongly linear. The resistive element 204 may be made of a polysilicon or other suitable material.

Furthermore, in an embodiment of the invention, the resistive element 204 may be supported on a thin (e.g., a few hundred nanometers in thickness) temperature sensor diaphragm 206 made of silicon nitride or a like material. The other face of the temperature sensor diaphragm 206 may form one side (or a portion thereof) of a vacuum cavity. In such an embodiment, the resistive element is relatively thermally isolated and there is little heat transfer between the resistive element and other elements of the MEMS sensor package 101.

The flow rate sensor may include a wire 205 through which electrical power of a known current and voltage may be passed. The wire 205 may be made of polysilicon or another suitable material. The wire 205 may be coupled to a conductor 207 on each end. The electrical current may raise the temperature of the wire 205 above the temperature of the surrounding fluid. As fluid passes over the heated wire, heat is dissipated to the surrounding fluid at a rate determined by the thermal properties of the fluid (specific heat, viscosity, etc.) and the fluid flow rate. The temperature of the wire 205 resulting from the net flow of energy into or out of the wire 205 may correspond to a resistance of the wire 205. By measuring the resistance of the wire 205, the amount of heat transferred to the fluid from the wire 205 can be determined. Since the thermal properties of the fluid are known, the flow rate of the fluid across the front face of the flow rate sensor can be calculated.

The amount of electrical current that must be passed through the wire 205 may depend upon the material of which the wire 205 is made and the configuration of the flow rate sensor 201 (e.g., how the wire 205 is supported). If, for example, the wire 205 is supported on a thin flow rate sensor diaphragm 208 over a vacuum cavity (as described earlier with respect to the temperature sensor 202), then it may be possible to supply the wire 205 with minimal electrical power and still achieve sufficient voltage drops to produce accurate flow rate measurements. For example, an electrical current of about 1 to 2 milliamperes may be passed through the wire at a voltage of about 2 Volts.

Figure 4:
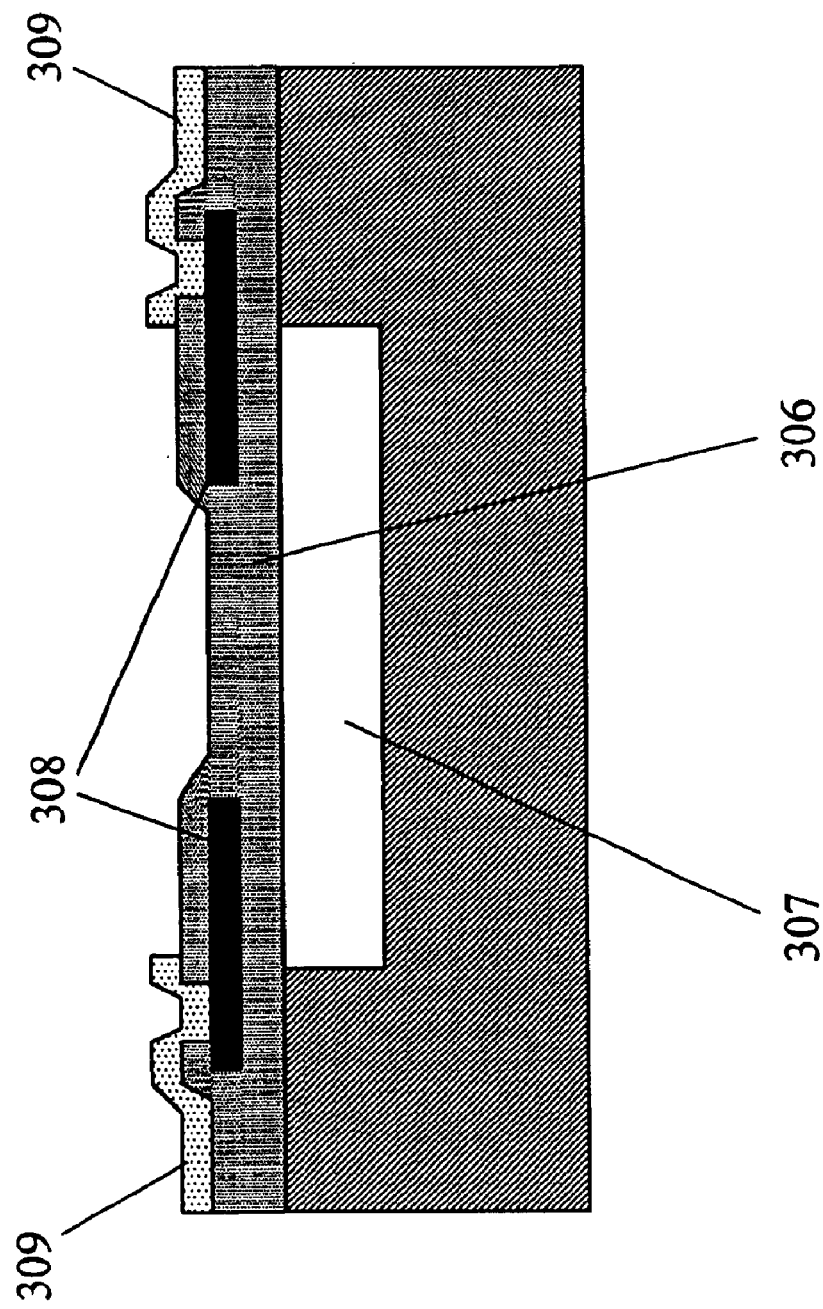
FIG. 4 illustrates a cross-sectional view of a pressure sensor that may be used in an embodiment of the invention.

Similarly, the pressure sensor 203 may include a diaphragm 306 made of a thin layer of a flexible material. In the embodiment shown in FIG. 4, the pressure sensor diaphragm 306 may be attached over a pressure reference chamber 307 so as to form an air- and fluid-tight seal between the pressure reference chamber 307 and the fluid. The pressure reference chamber 307 may contain a vacuum, or a gas or liquid at a known pressure. The difference between the fluid pressure and the pressure inside the pressure reference chamber 307 may cause the pressure sensor diaphragm 306 to deflect. One or more piezoelectric element(s) 308 may be attached to the surface of the pressure sensor diaphragm 306 or embedded within the pressure sensor diaphragm 306 so that as the pressure sensor diaphragm 306 deflects and stretches, the resulting strain on the piezoelectric element(s) 308 alters its resistance. The piezoelectric element(s) 308 may be made of polysilicon. The piezoelectric element(s) 308 may be electrically coupled by a metallic lead(s) 309 as a branch or branches of a bridge circuit and reference resistances may be attached to the remaining branches. The output voltage of the bridge circuit may be measured to determine the amount of strain on the piezoelectric element(s) 308, and thus, the pressure difference between the fluid and the pressure reference chamber 307.

In embodiments of the invention in which the flow rate sensor 201 uses thermal characteristics of the fluid flow to measure flow rate, it may be preferable to use a configuration in which the temperature sensor 202 and the pressure sensor 203 are not downstream from the fluid flow sensor 201. Heating the wire 205 of the flow rate sensor 201 and transferring at least some thermal energy from the wire 205 to the fluid flowing past the flow rate sensor 201 will raise the temperature and possibly affect other flow characteristics of at least some of the fluid downstream from the flow rate sensor 201. For example, if the temperature sensor 202 is downstream from the flow rate sensor 201, the measurements from the temperature sensor may be elevated and not reflective of the temperature of the majority of the fluid. However, in other embodiments of the invention, particularly those in which the flow rate sensor does not rely on thermal characteristics of the fluid, these restrictions on sensor placement may not apply.

In embodiments of the filter module having two or more sensor components 5, readings from the pressure sensors from each sensor component may be used to calculate the differential pressure across the filter element. Alternatively, the filter module may have a single sensor component 5 with a differential pressure MEMS sensor. In such an embodiment, the differential pressure sensor may be directly exposed to a first point in the fluid flow along a first face. The pressure associated with a second point in the fluid flow may be applied to a back face.

Measurements from the temperature sensor 202 may be used to calibrate the measurements from the remaining sensors. For example, the amount of energy supplied to the wire 205 in the fluid sensor may be changed depending on the measured fluid temperature to ensure that there is a sufficient difference in temperature between the wire 205 and the fluid to be able to measure the amount of energy removed from the wire 205 by the fluid flow. Moreover, the base (unstrained) resistance value of the piezoelectric element(s) 308 or the strain characteristics of the pressure sensor diaphragm 306 may depend upon the temperature of the fluid flow.

Based on the MEMS sensor package 101 measurement data or data related thereto that may be output by the processor 107, a computer or other data processing device 500 may be used to predict the remaining service life of the filter. The remaining service life may be the amount of time left before the filter will need to be replaced or reconditioned by backflushing or some other restorative procedure. It may be important to predict the remaining service life of a filter element in applications in which the filter will be required to remain in service for known periods of time. For example, for filtration systems used on aircraft, a filter may be required to remain in service throughout the duration of a flight. Or in power plant systems, a filter may be required to remain in service until the next scheduled plant outage.

Figure 5:
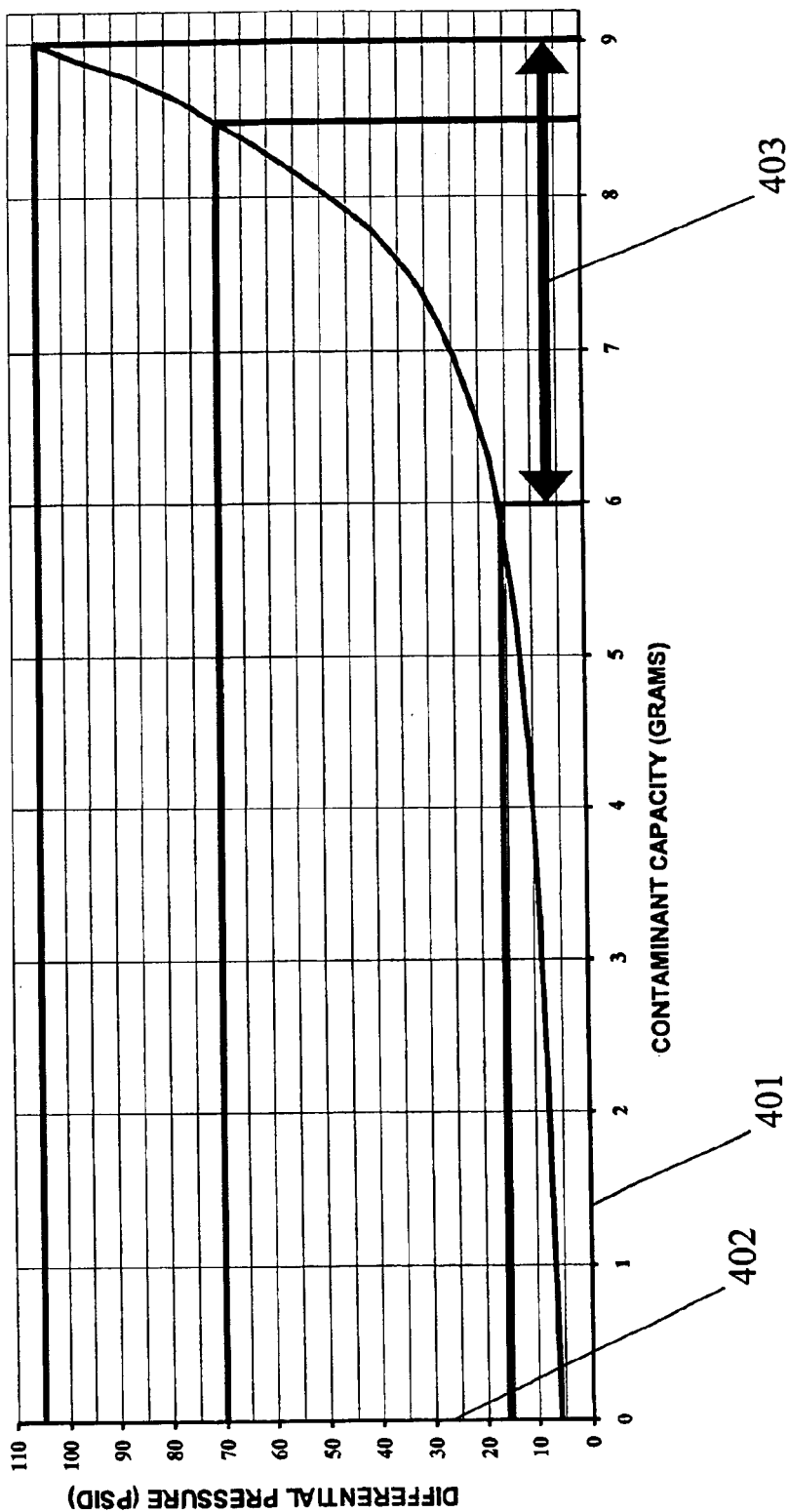
FIG. 5 shows an embodiment of filter life predictive data that may be used according to the present invention.

The remaining service life may be predicted based on filter characteristic data which relates the differential pressure across the filter element 2 with the amount of contaminant removed by the filter element 2. For example, FIG. 5 is a chart showing the typical relationship between differential pressure and amount of removed contaminant according to an embodiment of the invention. As the aggregate amount of contaminant removed from the fluid by the filter element 2 (the X-axis, 401) increases, the differential pressure across the filter element 2 (the Y-axis, 402) increases exponentially. The data processing device 500 may ascertain the differential pressure across the filter element from the MEMS sensor package 101 measurement data or data related thereto. The data processing device 500 may then use a chart or mathematical model to correlate the differential pressure to an amount of contaminant removed. If this correlation is performed for multiple differential pressure data, the data processing device 500 may be able to calculate a rate of contaminant removal and an remaining contaminant capacity 403. By dividing the remaining contaminant capacity by the rate of contaminant removal, the data processing device 500 may be able to predict the remaining service life of the filter element 2.

In an alternative embodiment, the data processing device 500 may store a differential pressure limit value which may correspond to a filter element being at a specified contaminant capacity. Based on past and current measurements of differential pressure, the data processing device 500 may calculate the rate at which the differential pressure is increasing and, accordingly, predict the amount of time needed for the differential pressure to reach the differential pressure limit value (the remaining service life).

The rate of contaminant removal may be affected by the fluid volume feed rate and the purity of the unfiltered fluid. In embodiments of the invention, the data processing device 500 may calculate the fluid volume feed rate from data related to the flow rate measurement data taken by the flow rate sensor 201.

The remaining service life may be calculated periodically or upon receiving a request from an operator. The calculated remaining service life may be recalculated with each new data point received by the data processing device 500. While the above discussion may have generally referred to the data processing device as separate from the processor 107, in embodiments of the invention, the processor 107 may be the data processing device.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A filtration health monitoring system comprising:
   a filter module including a filter element, said filter element having an inlet side, an outlet side, and a membrane separating said inlet side from said outlet side such that there exists a differential pressure across said membrane when said filter element is in service;
   a first micro-electro-mechanical systems (MEMS) pressure sensor disposed proximate said inlet side for measuring a first pressure on the inlet side;
   a second MEMS pressure sensor disposed proximate said outlet side for measuring a second pressure on the outlet side; and
   a processing device, said device being configured to:
      receive measurement data from said first and second MEMS pressure sensors;
      calculate the differential pressure across said membrane based on said measurement data;
      calculate a remaining contaminant capacity of the filter element based on a correlation of said differential pressure to an amount of contaminant removed by said filter element;
      calculate a rate of contaminant removal; and
      determine the remaining service life of said filter element.

2. The system of claim 1, wherein calculation of said rate of contaminant removal includes measurement of a fluid volume feed rate.

3. The system of claim 1, wherein the processing device receives said measurement data in real time.

4. The system of claim 1, wherein said measurement data is communicated to the processing device wirelessly.

5. The system of claim 1, wherein each of said MEMS sensors is contained within a respective sensor component, each said respective sensor component being coupled to said filter module and including a respective internal processor.

6. The system of claim 5, wherein the measurement data is communicated from each said MEMS sensor to each said respective processor, and from each respective processor to the processing device.

7. The system of claim 6, wherein said measurement data is communicated from each respective processor to the processing device wirelessly.

8. The system of claim 5, wherein said processing device is located outside said filter module.

9. The system of claim 5, wherein each of said first and second MEMS sensors is configured to take a measurement upon receiving a signal from said respective processor.

10. The system of claim 1, wherein at least one of said first and second MEMS sensors is in contact with a fluid being filtered through said filter element.

11. The system of claim 10, wherein said at least one MEMS sensor is flush with said fluid.

12. A filtration health monitoring system comprising:
   a filter module including a filter element, said filter element having an inlet side, an outlet side, and a membrane separating said inlet side from said outlet side such that there exists a differential pressure across said membrane when said filter element is in service;
   a first micro-electro-mechanical systems (MEMS) pressure sensor disposed proximate said inlet side for measuring a first pressure on the inlet side;
   a second MEMS pressure sensor disposed proximate said outlet side for measuring a second pressure on the outlet side; and
   a processing device, said device being configured to:
      receive measurement data from said first and second MEMS pressure sensors;
      calculate the differential pressure across said membrane based on said measurement data;
      calculate a rate of change of said differential pressure; and
      determine the remaining service life of said filter element based on a differential pressure limit.

13. The system of claim 12, wherein the processing device receives said measurement data in real time.

14. The system of claim 12, wherein said measurement data is communicated to the processing device wirelessly.

15. The system of claim 12, wherein each of said MEMS sensors is contained within a respective sensor component, each said respective sensor component being coupled to said filter module and including a respective internal processor.

16. The system of claim 15, wherein the measurement data is communicated from each said MEMS sensor to each said respective processor, and from each respective processor to the processing device.

17. The system of claim 16, wherein said measurement data is communicated from each respective processor to the processing device wirelessly.

18. The system of claim 15, wherein said processing device is located outside said filter module.

19. The system of claim 15, wherein each of said first and second MEMS sensors is configured to take a measurement upon receiving a signal from said respective processor.

20. The system of claim 12, wherein at least one of said first and second MEMS sensors is in contact with a fluid being filtered through said filter element.

21. The system of claim 20, wherein said at least one MEMS sensor is flush with said fluid.

22. A filtration health monitoring system comprising:
a filter module including a filter element, said filter element having an inlet side, an outlet side, and a membrane separating said inlet side from said outlet side such that there exists a differential pressure across said membrane when said filter element is in service;
a micro-electro-mechanical systems (MEMS) differential pressure sensor disposed proximate at least one of said inlet side and said outlet side for measuring said differential pressure; and
a processing device, said device being configured to:
receive differential pressure measurement data from said MEMS sensor;
calculate a remaining contaminant capacity of the filter element based on a correlation of said differential pressure to an amount of contaminant removed by said filter element;
calculate a rate of contaminant removal; and
determine the remaining service life of said filter element.

23. The system of claim 22, wherein said MEMS sensor and said processing device are disposed within a sensor component coupled to the filter module.

24. The system of claim 22, wherein said MEMS sensor is contained within a sensor component, said processing device is located outside said sensor component, and the sensor component is coupled to the filter module.

25. The system of claim 22, wherein calculation of said rate of contaminant removal includes measurement of a fluid volume feed rate.

26. The system of claim 22, wherein the processing device receives said measurement data in real time.

27. The system of claim 22, wherein said measurement data is communicated to the processing device wirelessly.

28. The system of claim 22, wherein said MEMS sensor is contained within a sensor component, said sensor component being coupled to said filter module and including an internal processor.

29. The system of claim 28, wherein the measurement data is communicated from the MEMS sensor to the processor, and from the processor to the processing device.

30. The system of claim 29, wherein the measurement data is communicated from the processor to the processing device wirelessly.

31. The system of claim 28, wherein the MEMS sensor is configured to take a measurement upon receiving a signal from said processor.

32. The system of claim 22, wherein the MEMS sensor is in contact with a fluid being filtered through said filter element.

33. The system of claim 32, wherein said MEMS sensor is flush with said fluid.

34. A filtration health monitoring system comprising:
a filter module including a filter element, said filter element having an inlet side, an outlet side, and a membrane separating said inlet side from said outlet side such that there exists a differential pressure across said membrane when said filter element is in service;
a micro-electro-mechanical systems (MEMS) differential pressure sensor disposed proximate at least one of said inlet side and said outlet side for measuring said differential pressure; and
a processing device, said device being configured to:
receive differential pressure measurement data from said MEMS sensor;
calculate a rate of change of said differential pressure; and
determine the remaining service life of said filter element based on a differential pressure limit.

35. The system of claim 34, wherein said MEMS sensor and said processing device are disposed within a sensor component coupled to the filter module.

36. The system of claim 34, wherein said MEMS sensor is contained within a sensor component, said processing device is located outside said sensor component, and the sensor component is coupled to the filter module.

37. The system of claim 34, wherein the processing device receives said measurement data in real time.

38. The system of claim 34, wherein said measurement data is communicated to the processing device wirelessly.

39. The system of claim 34, wherein said MEMS sensor is contained within a sensor component, said sensor component being coupled to said filter module and including an internal processor.

40. The system of claim 39, wherein the measurement data is communicated from the MEMS sensor to the processor, and from the processor to the processing device.

41. The system of claim 40, wherein the measurement data is communicated from the processor to the processing device wirelessly.

42. The system of claim 39, wherein the MEMS sensor is configured to take a measurement upon receiving a signal from said processor.

43. The system of claim 34, wherein the MEMS sensor is in contact with a fluid being filtered through said filter element.

44. The system of claim 43, wherein said MEMS sensor is flush with said fluid.

* * * * *